United States Patent [19]

Gordon et al.

[11] 4,402,935

[45] Sep. 6, 1983

[54] MOISTURIZING NAIL POLISH COMPOSITION

[75] Inventors: Harry W. Gordon, Wantagh; Herbert R. Farrell, Hempstead, both of N.Y.

[73] Assignee: Del Laboratories, Inc., Farmingdale, N.Y.

[21] Appl. No.: 369,591

[22] Filed: Apr. 19, 1982

Related U.S. Application Data

[63] Continuation of Ser. No. 254,731, Apr. 16, 1981.

[51] Int. Cl.$^3$ .............................................. A61K 7/04
[52] U.S. Cl. .................................................... 424/61
[58] Field of Search ........................................ 424/61

[56] References Cited

U.S. PATENT DOCUMENTS

| | | | |
|---|---|---|---|
| 3,422,185 | 1/1969 | Kuritzkes | 424/61 |
| 4,126,144 | 11/1978 | Duarte | 424/61 |
| 4,283,324 | 8/1981 | Duffy | 424/61 |

OTHER PUBLICATIONS

Balsam et al., *Cosmetic Science and Technology*, N.Y., Wiley Interscience, vol. II, 1972, pp. 521–530.
Gregory, *Uses and Applications of Chemicals and Related Materials*, N.Y., Reinhold Publishing Corporation, 1939, p. 630.

*Primary Examiner*—Delbert R. Phillips
*Assistant Examiner*—F. T. Moezic
*Attorney, Agent, or Firm*—Kirschstein, Kirschstein, Ottinger & Cobrin

[57] ABSTRACT

An improved nail polish composition for application to human nails which allows a polished nail to retain and absorb moisture thereby preventing brittleness and breakage of polished nails. Water and urea are used in the composition to impart moisture to the polished nail and polyvinyl butyral resin is used to harden the nail polish composition which is softened by the addition of water and to increase the adhesion of the nail polish composition to the nail.

5 Claims, No Drawings

MOISTURIZING NAIL POLISH COMPOSITION

This is a continuation, of application Ser. No. 254,731 filed Apr. 16, 1981.

BACKGROUND OF THE INVENTION

1. Field of the Invention

This invention relates to a nail polish composition which imparts moisture upon application to human nails.

2. Description of the Prior Art

It has long been recognized that when nail polish is applied to a human nail, the nail becomes dry and brittle. The polish draws out moisture from the nail and prevents moisture from being absorbed by the nail.

Nail polishes have been proposed which contain water. But no nitrocellulose polishes have been suggested which contain water, urea, and polyvinyl butyral resin.

SUMMARY OF THE INVENTION

Objects of the Invention

It is one of the objects of the invention to provide a nail polish composition which eliminates the drawbacks of the prior art nail polishes.

It is another object of the invention to provide a nail polish composition which prevents the polished nail from becoming dry and brittle.

It is a further object of the invention to provide a nail polish composition which moisturizes the human nail.

Yet a further object of the invention is to provide a nail polish composition which although softening the nail, forms a hard and durable lacquer coat.

A further object of the invention is to provide a nail polish composition containing water but which does not have a cloudy appearance due to the formation of precipitates.

Other objects of the invention in part will be obvious and in part will be pointed out hereinafter.

BRIEF DESCRIPTION OF THE INVENTION

In keeping with these objects, and others which will become apparent hereinafter, one feature of this invention resides, briefly stated, in an improved nail polish composition which moisturizes a polished human nail. A conventional liquid nail polish composition includes: nitrocellulose, one or more plasticizers, one or more hardeners, and a solvent system. The ingredients typically are ethyl acetate, isopropyl alcohol, butyl acetate, butyl alcohol, toluene, toluene sulfonamide/formaldehyde resin, dibutyl phthalate, camphor, nitrocellulose, and an ultra violet absorber. The improved polish additionally contains as the improvement, a combination of ingredients essentially constituting polyvinyl butyral resin, water and urea.

Both the water and the urea serves to moisturize the nail. The urea aids in the absorption of the water into the nail. The polyvinyl butyral resin is used to harden the nail polish coating which is softened by the addition of water. Further, the polyvinyl butyral resin increases the adhesion of the nail polish coating to the nail.

There are preferred weight percentages of polyvinyl butyral resin, water, and urea in the improved composition. For example, if too much water is used the wearability of the nail polish coating is adversely affected and precipitates are formed in the nail polish composition. If the percentage of water is too low, the moisturizing property of the nail polish composition is adversely affected.

DETAILED DESCRIPTION OF THE PREFERRED EMBODIMENT

Set forth below are components of a typical conventional nail polish composition to which the aforementioned ingredients are added to provide a moisturizing function.

| Ingredient | | Example I Preferred weight by percentage of liquid nail polish composition | Typical ranges |
|---|---|---|---|
| Ethyl Acetate | | 36.7% | 20%–40% |
| Isopropyl Alcohol | | 24.2% | 15%–30% |
| Butyl Acetate | (solvent system) | 9.9% | 3%–25% |
| Butyl Alcohol | | 1.4% | 0.5%–10% |
| Toluene | | 7.4% | 2%–30% |
| Toluene Sulfonamide/Formaldehyde Resin (hardener) | | 14.4% | 5%–20% |
| Camphor | (plasticizers) | 0.9% | 0.5%–8% |
| Dibutyl Phthalate | | 1.2% | 0.5%–8% |
| Nitrocellulose (film former) | | 3.6% | 2%–15% |
| Ultra violet absorber | | 0.1% | 0.1%–0.5% |

The water may be deionized or tap water. The polyvinyl butyral resin, the water, and the urea are added in a preferred weight percentage. However, there is an acceptable weight percent range. If these ingredients are used in an amount falling within said weight percentage range, a commercially acceptable product is obtained.

A preferred weight percent and an acceptable weight percentage range are as follows:

| Ingredient | Preferred weight by percent of liquid nail polish composition (Example II) | Weight percent range of liquid nail polish composition |
|---|---|---|
| Water | 6% | 3%–10% |
| Urea | 0.1% | 0.02%–0.5% |
| Polyvinyl butyral resin | 2.2% | 1%–3% |

Urea, or any precursor thereof, can be used in the moisturizing composition. Urea is an organic compound with the chemical formula:

$$NH_2CONH_2$$

It has a molecular weight of 60.06 and a melting point of 135° C. It is a weakly basic compound.

Some properties of polyvinyl butyral resins are:

| Property | Units | ASTM method | |
|---|---|---|---|
| Tensile strength | | | |
| Yield | $10^3$ psi | D638-58T | 6.3–7.3 |
| Break | $10^3$ psi | D638-58T | 5.6–6.6 |
| Elongation | | | |
| Yield | % | D638-58T | 8 |
| Break | % | D638-58T | 110 |
| Modulus of elasticity (apparent) | $10^5$ psi | D638-58T | 3.1–3.2 |
| Flexural strength, yield | $10^3$ psi | D790-59T | 11–12 |
| Hardness, Rockwell | | | |

-continued

| Property | Units | ASTM method | |
|---|---|---|---|
| M | — | D785-51 | 110 |
| E | — | D785-51 | 20 |
| Impact strength Izod, notched ½" × ½" | ft.lb/in | D256-56 | 0.7 |

It has been found that when the nail polish composition of this invention is applied to human nails, the nails have a higher moisture content than nails polished with a conventional nail polish composition. Nails polished with the moisturizing composition of this invention are less brittle and do not break as frequently as nails polished with a conventional nail polish composition.

In tests of the moisturizing composition of this invention versus a conventional clear nail polish, the results indicated that nails coated with this moisturizing composition had a higher percentage of moisture than nails coated with a standard commercially available polish.

The first fourteen subjects on the test results of Table 1, were treated as follows: the first seven had the nails on their right hands coated with the moisturizing composition (the liquid nail polish of Example I mixed with the moisturizer additive of Example II) and the nails on their left hands coated with a conventional liquid clear polish (Example I). The second group of seven had the nails of their left hands coated with said moisturizing composition and the nails on their right hands coated with said standard clear polish.

The last six subjects of Table 1 had the nails of one hand coated with the nail polish of Example 1 mixed with the moisturizing additive of Example II and the nails of the other hand coated with the clear nail polish of Example I. The nails of both hands then were overcoated with the nail polish of Example I mixed with color.

The moisture content of the nails of all 20 subjects were determined by the following procedure: The nails were allowed to dry for 24 hours. It was previously determined that in this period of time the nail polish coats were fully dried. Then the nails from both hands of the subjects were clipped and weighed. The nail clippings next were placed in an oven maintained at a temperature of about 100° C. in order to evaporate moisture in the clippings. Sample nail clippings were periodically removed from the oven to determine when their weight remained constant to establish substantially complete removal of moisture. This occured in approximately 1¼ hours. The nail clippings then were weighed a second time. The difference in weight between the weight after the 24 hour period and the weight after the oven drying period was taken as the moisture content of the clippings before oven drying. The moisture content of the nail clippings to which the non-moisturizing coats were applied was used as a control. Results are set forth in the following Table 1:

TABLE I

| SUBJECT | MOISTURE CONTENT OF NAILS W/ STANDARD CLEAR NAIL POLISH (% BY WEIGHT) | MOISTURE CONTENT OF NAILS W/ MOISTURIZING BASE COAT (% BY WEIGHT) | % INCREASE IN MOISTURE CONTENT |
|---|---|---|---|
| S.A. | 5.0 | 6.17 | 23.4 |
| A.B. | 4.8 | 5.87 | 22.3 |
| D.F. | 5.1 | 6.19 | 21.4 |
| C.H. | 5.3 | 6.17 | 16.4 |
| R.K. | 5.2 | 6.275 | 20.67 |
| J.L. | 4.9 | 5.96 | 21.6 |
| K.M. | 4.5 | 5.45 | 21.1 |
| B.P. | 5.2 | 6.37 | 22.5 |
| M.S. | 5.3 | 6.34 | 19.6 |
| V.S. | 5.1 | 6.08 | 19.2 |
| A.W. | 5.3 | 6.5 | 22.6 |
| G.H. | 4.9 | 5.4 | 10.2 |
| M.C. | 5.2 | 6.46 | 24.23 |
| L.F. | 4.9 | 5.72 | 16.7 |

| SUBJECT | MOISTURE CONTENT OF NAILS W/ STANDARD CLEAR NAIL POLISH AND REVLON OVERCOAT (% BY WEIGHT) | MOISTURE CONTENT OF NAILS W/ MOISTURIZING BASE COAT AND REVLON OVERCOAT (% BY WEIGHT) | % INCREASE IN MOISTURE CONTENT |
|---|---|---|---|
| J.S. | 5.2 | 6.23 | 19.8 |
| A.J. | 5.3 | 5.94 | 12.1 |
| C.Y. | 5.1 | 6.22 | 22.0 |
| L.R. | 4.8 | 5.6 | 16.7 |
| A.L. | 4.4 | 5.2 | 18.2 |
| P.W. | 4.9 | 5.88 | 20.0 |

The moisturizing composition of this invention may be any liquid nail polish composition which is applied directly to the nail, i.e. as a colorless "base" coat or as a colored coat. In a preferred embodiment, the moisturizing polish is a base coat and it is intended that additional coats of polish will be applied over said base coat.

It has been found that the wearability of the nail polish composition is not adversely affected by the inclusion of water in the composition. As heretofore explained, it is believed that the polyvinyl butyral resin preserves the wearability of the composition by hardening the polish which has been softened by the addition of water.

Tests were run to determine wearability of the moisturizing liquid nail polish composition in comparison with a standard liquid nail polish composition, specifically the liquid polish composition of Example I. The tests were conducted as follows: Fourteen women were used as subjects. They were employed in light to heavy manual jobs such as typing and factory work. Each woman had applied to alternating nails of both her hands; (a) a base coat of Example 1, overcoated with two coats of a nail polish of Example I in which a color had been mixed; and (b) a moisturizing base coat constituting a mixture of Example I and Example II, overcoated with two coats of a nail polish of Example I in which a color had been mixed. The nails of these women were examined at the end of the first day after application and then again at the end of the second day after application. Wear was evaluated by ascribing a rating to the individual nails on the fingers of both hands, ranging from 0–5, 0 being no visible chipping and wear, 1 being a slight chipping and wear and so on up to 5 which was indicative of heavy chipping and wear. After the first day the nails which had the non-moisturizing base coating of Example I, plus two overcoats of Example I with color mixed in, had a total wear rating for all such nails (based on the wear rating above) of 80, in contrast to the total wear rating for the nails having the moisturizing base coat of Example I mixed with Example II and overcoated with two coats of Example I with color mixed in of 79. At the end of two days, the total wear rating for the nails having the standard nail polish overcoated with two coats of a colored nail polish was 109 as compared to 104 for the nails coated with a moisturizing base coat overcoated with two coats of a colored nail polish. Thus, the addition of the moisturizing constituents did not increase chipping or reduce wearability. Further, the percentage of water in the composition was low enough so that precipitates were not formed.

As various possible embodiments might be made of the present invention and as various changes might be made in the embodiment set forth, it should be understood that all matters herein described are to be interpreted as illustrative and not in a limiting sense.

We claim:

1. An improved nail polish composition for application to human nails, the composition consisting essentially of a conventional nail polish composition containing:

| Ingredient | Quantity by Weight in %'s of the conventional nail polish composition |
|---|---|
| Ethyl acetate (solvent system) | 36.7% |
| Isopropyl alcohol | 24.2% |
| Butyl acetate | 9.9% |
| Butyl alcohol | 1.4% |
| Toluene | 7.4% |
| Toluene sulfonamide/formaldehyde resin (hardener) | 14.4% |
| Camphor (plasticizers) | 0.9% |
| Dibutyl phthalate | 1.2% |
| Nitrocellulose (film former) | 3.6% |
| to which is added an improvement containing: | |
| Water | 6% |
| Urea | 0.1% |
| Polyvinyl butyral resin | 2.2% |

2. An improved liquid nail polish composition for application to human nails constituting a conventional liquid nail polish of the type essentially including 2–15 percent nitrocellulose, a plasticizer, including 0.5–8 percent camphor and 0.5–8 percent dibutyl phthalate, a hardener constituting 5–20 percent toluene sulfonamide/formaldehyde resin, and a solvent system including 20–40 percent ethyl acetate, 15–30 percent isopropyl alcohol, 3–25 percent butyl acetate, 0.5–10 percent butyl alcohol and 2–30 percent toluene, all the percentages being by weight of the conventional nail polish, said conventional nail polish having admixed therewith a moisturizing composition essentially consisting of:
(a) 1–3 percent polyvinyl butyral resin;
(b) 3–10 percent water; and
(c) 0.02–0.5 percent urea,
the percentages of the moisturizing composition being percentages by weight of the improved liquid nail polish composition, whereby the improved liquid nail polish composition supplies moisture to a polished nail.

3. The improved nail polish composition of claim 2, wherein the water is present in an amount of about 6 percent by weight of the improved liquid nail polish composition.

4. The improved nail polish composition of claim 2, wherein urea is present in an amount of about 0.1 percent of the improved liquid nail polish composition.

5. The improved nail polish composition of claim 2, wherein the polyvinyl butyral resin is present in an amount of about 2.2 percent by weight of the improved liquid nail polish composition.

* * * * *